United States Patent
Schär et al.

(10) Patent No.: US 6,866,664 B2
(45) Date of Patent: Mar. 15, 2005

(54) DEVICE FOR RELEASABLY CLAMPING A LONGITUDINAL MEMBER WITHIN A SURGICAL IMPLANT

(75) Inventors: Manuel Schär, Muttenz (CH); David Gerber, Arbon (CH); Fridolin Schläpfer, Glarus (CH)

(73) Assignee: Synthes (U.S.A.), Paoli, PA (US)

( * ) Notice: Subject to any disclaimer, the term of this patent is extended or adjusted under 35 U.S.C. 154(b) by 104 days.

(21) Appl. No.: 10/193,987

(22) Filed: Jul. 15, 2002

(65) Prior Publication Data

US 2003/0028192 A1 Feb. 6, 2003

Related U.S. Application Data

(63) Continuation of application No. PCT/CH00/00018, filed on Jan. 13, 2000.

(51) Int. Cl.[7] .......................... A61B 17/56; A61B 17/58; A61F 2/30
(52) U.S. Cl. ....................................................... 606/61
(58) Field of Search .............................. 606/53, 60, 61, 606/72, 73, 63

(56) References Cited

U.S. PATENT DOCUMENTS

| | | | | |
|---|---|---|---|---|
| 5,275,600 A | * | 1/1994 | Allard et al. .................. | 606/61 |
| 5,312,405 A | * | 5/1994 | Korotko et al. ............... | 606/61 |
| 5,344,457 A | * | 9/1994 | Pilliar et al. .................. | 606/60 |
| 5,630,817 A | * | 5/1997 | Rokegem et al. ............. | 606/61 |
| 5,702,393 A | | 12/1997 | Pfaifer ......................... | 606/61 |
| 5,752,955 A | * | 5/1998 | Errico .......................... | 606/61 |
| 5,863,293 A | * | 1/1999 | Richelsoph ................... | 606/61 |
| 5,947,966 A | * | 9/1999 | Drewry et al. ................ | 606/61 |
| 5,964,760 A | * | 10/1999 | Richelsoph ................... | 606/61 |
| 6,074,391 A | * | 6/2000 | Metz-Stavenhagen et al. ............................ | 606/61 |
| 6,139,549 A | * | 10/2000 | Keller .......................... | 606/61 |
| 6,171,311 B1 | | 1/2001 | Richelsoph ................... | 606/61 |
| 6,264,658 B1 | * | 7/2001 | Lee et al. ...................... | 606/61 |
| 6,283,967 B1 | * | 9/2001 | Troxell et al. ................ | 606/61 |
| 6,371,957 B1 | * | 4/2002 | Amrein et al. ................ | 606/61 |
| 6,413,257 B1 | * | 7/2002 | Lin et al. ...................... | 606/61 |
| 6,752,807 B2 | * | 6/2004 | Lin et al. ...................... | 606/61 |

FOREIGN PATENT DOCUMENTS

| | | |
|---|---|---|
| EP | 0 778 007 | 6/1997 |
| EP | 0 836 836 A2 | 4/1998 |
| FR | 2 736 535 | 1/1997 |
| WO | WO 99/09901 | 3/1999 |

\* cited by examiner

Primary Examiner—Kevin Shaver
Assistant Examiner—Anuradha Ramana
(74) Attorney, Agent, or Firm—Jones Day

(57) ABSTRACT

A device for releasably clamping and connecting a longitudinal member within a surgical implant includes at least one yoke-like connecting body with a through-bore, coupling means arranged on the connecting body for fastening the connecting body to a further part of the implant, a yoke-like clamping body which can slide in the through-bore and has resilient side walls and a through-opening for receiving the longitudinal member, and fixation means. A wedging effect produced by elevations on side walls of the clamping body retains the longitudinal member in the through-opening.

23 Claims, 5 Drawing Sheets

DEVICE FOR RELEASABLY CLAMPING A LONGITUDINAL MEMBER WITHIN A SURGICAL IMPLANT

CROSS-REFERENCE TO RELATED APPLICATIONS

This application is a continuation of the U.S. National Stage designation of co-pending International Patent Application PCT/CH00/00018, filed Jan. 13, 2000, the entire content of which is expressly incorporated herein by reference thereto.

FIELD OF THE INVENTION

The invention relates to a device for releasably clamping and connecting a longitudinal member within a surgical implant in the body of human or animal.

BACKGROUND OF THE INVENTION

Surgical implants as used for bone fixation or specifically for spinal fixation often contain one or more longitudinal members, to which the bone fixation elements or, specifically in the case of spinal fixation, the pedicle screws are fastened and consequently are fixed with respect to one another in a longitudinal direction. For stiffening an implant as a whole, containing a plurality of longitudinal members, the longitudinal members are connected to one another by means of transverse connectors, which are attached transversely with respect to the longitudinal members between the latter.

Some devices for connecting longitudinal members within spinal column implants are already known from the prior art. These have the advantage that the implanted longitudinal members are considerably stiffened by the transverse connection by means of these devices. Thanks to the already known devices, it is also possible to implant the transverse connections at angles which deviate to a certain extent from a right angle.

Such a device for connecting longitudinal members is known for example from EP-A 0 836 836 to Richelsoph. The device disclosed therein for connecting longitudinal members within spinal column implants comprises a telescopic transverse connecting body with two bores for each receiving an insert, the two bores being provided at the opposite ends of the transverse connecting body. The transverse connecting body can be partly slipped over the longitudinal members running transversely with respect to the central axis of the connecting body.

A further connecting device of this kind is known from EP-A 0 778 007 to Pfaifer. This known device comprises a central body, a ring which can be pushed over the latter and a nut which can be screwed onto an external thread provided at the upper end of the central body. Transversely with respect to the longitudinal axis of the central body and transversely with respect to the central axis of the channel, a through-opening is provided in the central body for receiving a transverse rod. This transverse rod is received in a corresponding channel in the ring and fixed with respect to the device by clamping between the ring and nut.

A disadvantage of EP-A 0 778 007 to Pfaifer is that the longitudinal member can be arranged only within a small angular range, including right angles, with respect to the transverse connector.

The invention is intended to remedy this. The invention relates to a device for connecting rods and specifically also longitudinal members of spinal column implants, or else for connecting a rod to a further implant, for example to a bone anchorage element or a pedicle screw, with the following properties: simple handling; connection of longitudinal members which are not implanted in parallel; prevention of slipping of the rod connection after implantation; and making it possible for an implant as a whole to be very rigid, for example with longitudinal members that cannot twist after the fastening of the rod connections. Such a device may be used for releasably clamping and connecting a longitudinal member within a surgical implant in the body of a human or animal.

SUMMARY OF THE INVENTION

Advantageously, the device of the present invention prevents slipping of the rod connection after implantation, due to the force acting on the longitudinal member. In addition, the device of the present invention permits the connection of longitudinal members which are not implanted in parallel. Further, even when the device is subjected to significant torques such as by the longitudinal member or members, the implant as a whole has great rigidity.

The invention relates to a device for releasably clamping and connecting a longitudinal member within a surgical implant in the body of human or animal. The device includes at least one yoke-like connecting body formed with two side walls and a cross-piece, a central axis intersecting the cross-piece and running between the side walls, a free space lying between the cross-piece and side walls for receiving a longitudinal member transverse to the central axis, and a through-bore running coaxially with respect to the central axis and penetrating the connecting body. A coupling means, for example a transverse rod, is arranged on the outside of the yoke-like connecting body transverse to the central axis on at least one of the side walls for connection of the connecting body to a further part of the implant, for example a further device according to the invention, a bone anchorage element or a pedicle screw. Also, a yoke-like clamping body is provided, and can slide in the through-bore. The clamping body has side walls running parallel to the central axis in the region of the yoke and which are resilient transverse to the central axis and have free ends. A through-opening arranged between the side walls, corresponding to the free space, and penetrating the clamping body, has a longitudinal axis that runs transverse to the central axis and receives a longitudinal member. Fixation means can be placed on the connecting body coaxially with the central axis and opposite the free space, and can be connected to the clamping body in a screwable manner. The fixation means lock the longitudinal member and the clamping body within the connecting body. By tightening the fixation means, a tensile force can be exerted on the clamping body and directed coaxially with respect to the central axis. The side walls of the clamping body may be provided proximate their free ends with elevations directed towards the interior of the through-opening and the central axis, so that the through-opening has, in cross-section, a central angle of more than 180°. These elevations constrict the cross-section of the through-opening in such a way that the longitudinal member is secured in the direction of the central axis in the through-opening and, when the fixation means is tightened, the side walls are pressed against the wall of the through-bore by the compressive force of the longitudinal member on the elevations, exerted by at least one of the parts of the device moved in relation to the longitudinal member. As a result, when the fixation means is tightened, the longitudinal member and the clamping body are fixed at the same time in the connecting body.

When the fixation means is tightened, the clamping body can be moved with respect to the connecting body and the fixation means until the longitudinal member inserted in the through-opening comes to bear against one of these parts of the device moved in relation to the clamping body. The longitudinal member may be pressed against the elevations. The side walls of the clamping body may be pressed against the wall of the through-bore by the component of the compressive force directed perpendicularly with respect to the central axis and exerted by the longitudinal member on the elevations.

Thus, the clamping body can be brought into a first position in relation to the connecting body which allows the side walls to spring out transversely with respect to the central axis, so that a longitudinal member can be snapped into the through-opening coaxially with respect to the central axis. By tightening the fixation means, the clamping body can be brought into a second position, so that the cross section of the through-opening is reduced by at least one of the parts moved in relation to the clamping body to such an extent that a longitudinal member placed in the through-opening is pressed against the elevations. A wedging effect is thus produced on the elevations, and the side walls of the clamping body are pressed against the inner sides of the side walls of the connecting body.

In some embodiments, the through-opening has in cross-section a central angle of between 200° and 250°, while in other embodiments the through-opening has in cross-section a central angle of between 210° and 240°. The connecting body may have, in the direction of the central axis, an end on the clamping body side and an opposite end on the fixation means side, with a free space lying between the side walls and being open toward the end on the clamping body side. Thus, it is possible for the fixation means to exert a tensile force on the clamping body from the end of the connecting body on the fixation means side.

In an exemplary preferred embodiment of the device according to the present invention, corresponding serrations, the teeth of which run parallel to the central axis, are provided on the outside circumference of the clamping body and in the throughbore. These serrations permit the clamping body to be fitted in the connecting body at different rotational angles about the central axis and, on the other hand, do not permit the clamping body to twist with respect to the connecting body in the fitted and implanted state, even when relatively great torques occur through the longitudinal member fastened in the clamping body.

The fixation means is advantageously designed in such a way that a tensile force can be exerted on the clamping body from the end of the connecting body on the fixation means side. For this purpose, the clamping body is for example provided at its end on the fixation means side with an internal thread running coaxially with respect to the central axis, and the fixation means is formed as a locking screw with an external thread corresponding to the internal thread and the screw head of which at the end of the connecting body on the fixation means side is secured against movement in the direction of the central axis. The securing of the screw head is possible by mounting the screw head or a flange-shaped part thereof in a relief in the through-bore of the connecting body. As a result, the locking screw is secured against movements in the axial direction and continues to be freely rotatable.

In a further preferred embodiment of the device according to the present invention: the connecting body is designed in such a way that the locking screw penetrates into the connecting body in the direction of the central axis by a length X from the end on the fixation means side; the connecting body has a height H in the direction of the central axis between its end on the fixation means side and its end on the clamping body side; and the free space has a limitation transversely with respect to the central axis towards the cross-piece so that the free space has a depth T in the direction of the central axis between the end on the clamping body side and its upper limitation, lying in the direction of the end on the fixation means side. The following condition is met:

$$X > H - T$$

By satisfying this condition, it is ensured that only the end of the locking screw on the clamping body side is pressed from above onto the longitudinal member and presses the latter against the elevations on the side walls of the clamping body.

In a further exemplary preferred embodiment of the device according to the present invention: the connecting body is designed in such a way that the locking screw can penetrate into the connecting body in the direction of the central axis only by a length X from the end on the fixation means side; the connecting body has a height H in the direction of the central axis between its end on the fixation means side and its end on the clamping body side; and the free space has a limitation transversely with respect to the central axis towards the cross-piece so that the free space has a depth T in the direction of the central axis between the end on the clamping body side and its upper limitation, lying in the direction of the end on the fixation means side. The following condition is met:

$$X > H - T$$

By satisfying this condition, it is ensured that only the upper limitation of the free space is pressed from above onto the longitudinal member and presses the latter against the elevations on the side walls of the clamping body.

Instead of the fixation means being configured as a locking screw, it is also possible for the fixation means to be configured as a nut, which is screwed over a threaded pin correspondingly provided on the clamping body.

The through-opening preferably has a circular-cylindrical core with a diameter D, while the side faces bounding the elevations towards the through-opening have a distance A at right angles with respect to the central axis. The ratio A/D is between about 85% and about 98%, preferably between about 92% and about 98%. This configuration of the through-opening makes it possible, by the resilient side walls of the clamping body, for the longitudinal member to be snapped in and for the longitudinal member to be stable and fixed in the through-opening when the locking screw is tightened.

The configuration of wedge-shaped elevations allows the clamping force of the clamping body to be optimized within the through-bore in the connecting body. The elevations are designed in such a way that each elevation tapers parallel to the direction of the central axis and towards the interior core of the through-opening. The wedge shape of the elevations can also be achieved by a core of the through-opening having, for example, a cross section similar to a segment of a circle, with a central angle measured symmetrically with respect to the central axis of more than 180°.

In a further exemplary embodiment, the device according to the present invention comprises two connecting bodies each with a clamping body and each with a locking screw, the two connecting bodies being connected to one another by transverse rods which can be telescoped in one another. This exemplary embodiment of the device is suitable as a transverse connector between two longitudinal members, for example within a spinal column implant.

Instead of the telescopic transverse rods, sleeves may be provided which are attached to the connecting bodies as coupling means for displaceably receiving a single transverse rod.

The coupling means may include a sleeve with a bore arranged transversely with respect to the central axis for receiving a rod and a fastening screw may penetrate the sleeve to fix the rod in the bore.

In order that the longitudinal member can be inserted more easily into the through-opening from the entry in the direction of the central axis, the free ends of the clamping body may also be provided with centering jaws which are designed in such a way that the cross-section of the through-opening narrows from the entry at the free ends towards the elevations, thus making it possible for a longitudinal member to be centered and inserted into the through-opening in a simple manner. The centering jaws may taper toward the free ends in planes running parallel to a plane defined by the central axis and the longitudinal axis.

The coupling means may include a transverse rod arranged transverse to the central axis on the connecting body. Further application possibilities include that a connecting body can be connected by means of the transverse rod, for example, to a bone anchorage element or a pedicle screw.

The device may include two connecting bodies each having a clamping body and locking screw. The two connecting bodies may be connected by a rod which can be inserted into the bores of the sleeves and can be fixed by means of the fastening screws.

The invention and developments of the invention are explained in more detail below with reference to the partially schematic representations of several exemplary embodiments.

BRIEF DESCRIPTION OF THE DRAWINGS

Preferred features of the present invention are disclosed in the accompanying drawings, wherein similar reference characters denote similar elements throughout the several views, and wherein.

DETAILED DESCRIPTION OF PREFERRED EMBODIMENTS

Figure 1:
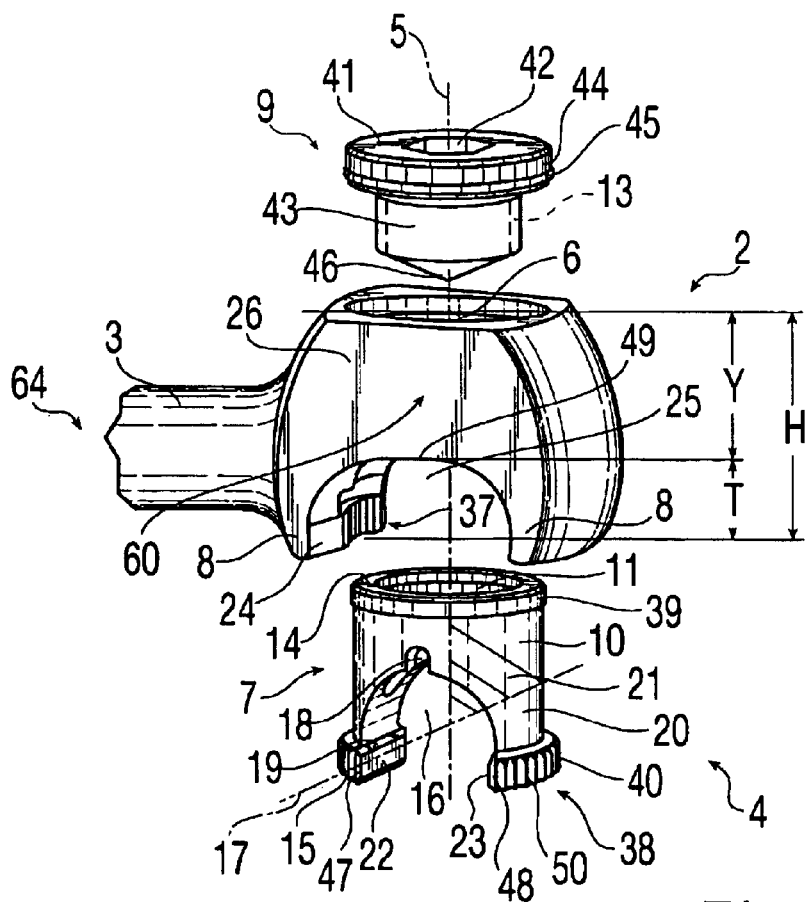
FIG. 1 shows a perspective view of an embodiment of a device according to the present invention.
Figure 2:
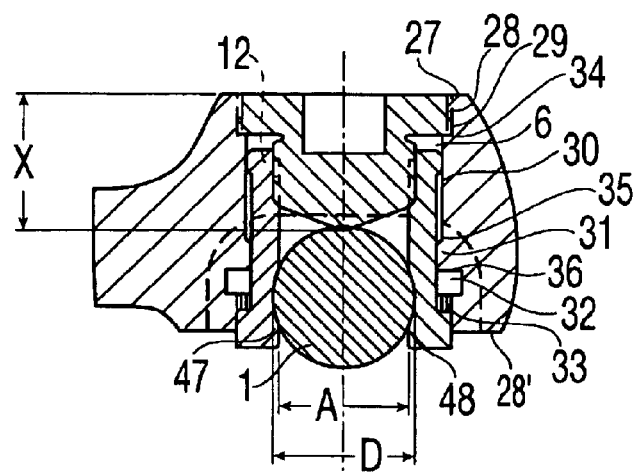
FIG. 2 shows a section through a variant of the embodiment of the device of FIG. 1.

With reference to FIGS. 1 and 2, an exemplary embodiment of a device according to the present invention is shown including a connecting element 4 between a longitudinal member 1 and a transverse rod 3. In this exemplary embodiment, connecting element 4 comprises a yoke-like connecting body 2 that is symmetrical with respect to a central axis 5 and has a through-bore 6 coaxially disposed on central axis 5. Connecting element 4 also includes a hollow-cylindrical clamping body 7 which is displaceable in through-bore 6 parallel to central axis 5, and a fixation means 9 for fixing longitudinal member 1 within the device.

Yoke-like connecting body 2 includes two side walls 8 that may run in the direction of central axis 5. A free space 25 is disposed between side walls 8, which have side faces 24 that are angulated to converge toward through-bore 6. As such, a longitudinal member 1 passing through free space 25 can be fastened within an angular range of between about 75° and about 105° with respect to an end face 26 of connecting body 2. Through-bore 6 is configured with portions 28, 29, 30, 31, 32, 33 having different diameters. Beginning at end 27 of connecting body 2, located on the side thereof which receives fixation means 9, a cylindrical portion 28 is provided and followed by a relief 29 that is followed by a portion 30 of a smaller diameter. A first shoulder 34 is produced, after which portion 30 is followed by a portion 31 having a smaller diameter, thereby producing a second shoulder 35. Portion 31 is followed by a second relief 32, which is finally followed by a portion 33 provided with a serration 37 that runs parallel to central axis 5. Portion 33 extends to end 28', located on the side of connecting body 2 which receives clamping body 7. The outside diameter of serrated portion 33 is greater than the diameter of portion 31, so that a third shoulder 36 is produced. Shoulders 34 and 35 serve as stops in the direction of end 28'. A locking screw 43, serving as fixation means 9, also serves as a stop in the direction of end 27. A transverse rod 3 is provided on the outside of the connecting body 2, and is disposed perpendicular to central axis 5. Transverse rod 3 permits connection of connecting element 4 to other parts of the implant as a whole.

The similarly yoke-like clamping body 7 comprises a hollow cylinder 10 disposed concentric with central axis 5. Hollow cylinder 10 has free ends 15, 50 on the side that receives longitudinal member 1, along with an upper end 14 on the side receiving fixation means 9. A through-opening 16 in hollow cylinder 10 has a longitudinal axis 17 disposed perpendicular to central axis 5. Through-opening 16 is constricted towards lower end 15 by means of wedge-like elevations 47 and 48, and tapers toward upper end 14. Thus, clamping body 7 is provided with a U-like shape, open towards the free ends 15, 50, with opposing side walls 19, 20 designed in the form of clamps around through-opening 16. The through-opening 16 is symmetrical with respect to plane 21, which is disposed on central axis 5 and contains longitudinal axis 17. A cylindrical core with the diameter D is formed by through-opening 16 for receiving longitudinal member 1. In addition, through-opening 16 is provided with a slit 18 extending toward upper end 14, as well as side faces 22, 23 proximate lower end 15 that form part of elevations 47, 48. The distance A, measured perpendicular to plane 21 between side faces 22, 23, as shown in FIG. 2, is smaller than the diameter D shown as the diameter of longitudinal member 1. In on exemplary embodiment, distance A is 95% of diameter D.

Clamping body 7 includes a portion 40 disposed proximate lower ends 15, 50 on the side that receives longitudinal member 1. Portion 40 includes a serration 38, which corresponds to serration 37 provided on connecting body 2. Proximate upper end 14 on the side receiving fixation means 9, clamping body 7 is provided with a portion 39 which has a greater outer diameter than the outer diameter of hollow cylinder 10. The diameter of portion 39 preferably corresponds to the inner diameter of connecting body 2 at portion 30. Thus, when clamping body 7 is fitted in connecting body 2, second shoulder 35 of connecting body 2 prevents clamping body 7 from sliding out of connecting body 2 in the direction of lower end 28'. In order to fit clamping body 7 in connection body 2, portion 39 of clamping body 7 is elastically deformed as it is pressed passed the smaller diameter of portion 31 of connecting body 2. Once pressed beyond portion 31, portion 39 of clamping body 7 springs back to its initial diameter and remains in portion 30.

Clamping body 7 is also prevented from sliding out of connecting body 2 in the direction of upper end 27 by locking screw 43. Furthermore, while matching serrations 37, 38 permit clamping body 7 to be fitted in connecting body 2 at different rotational angles about central axis 5, the serrations prevent twisting of clamping body 7 with respect to connecting body 2 once fitted therein, even when relatively great torques are applied by a longitudinal member 1 fastened in clamping body 7. Moreover, a bore 11 provided in clamping body 7 is provided with an internal thread 12 proximate upper end 14.

Fixation means 9, for example, may be a locking screw 43 with an external thread 13 corresponding to internal thread 12 in bore 11. Locking screw 43 is shown in FIG. 1 with a screw head 41 and a hexagon socket 42. Screw head 41 is cylindrically shaped and has two portions 44, 45, with portion 45 disposed closer to external thread 13 and having a larger diameter than portion 44. Thus, portion 45 may engage in relief 29 provided in connecting body 2 and once seated therein, locking screw 43 is positionally fixed on central axis 5 while being freely rotatable thereabout. In order to fit portion 45 of locking screw 43 in relief 29, portion 45 is pressed and elastically deformed passed the smaller diameter portion 28 of connecting body 2, and permitted to spring back to its initial diameter within relief 29.

The clamp-like and resilient side walls 19, 20 of clamping body 7 allow longitudinal member 1 to be snapped and retained therein from lower end 15. Once longitudinal member 1 has been placed in through-opening 16, the clamping body 7 may be drawn into through-bore 6 of connecting body 2 by tightening locking screw 43 until end 46 of locking screw 43 abuts longitudinal member 1. With further tightening of locking screw 43, the longitudinal member 1 is pressed against elevations 47, 48 with a force F. The circular cross section of longitudinal member 1 and the wedge shape of elevations 47, 48 have the effect that force F is also given a component acting perpendicular with respect to central axis 5. Thus, side walls 19, 20 are pressed away from central axis 5 toward through-bore 6 of the connecting body 2, and consequently clamping body 7 and longitudinal member 1 are fixed within connecting body 2. In order that end 46 of locking screw 43 abuts longitudinal member 1, rather than stopping at upper limitation 49 of free space 29, locking screw 43 must penetrate into connecting body 2 by a length X which is greater than the dimension Y which is obtained by the difference between the height H of the connecting body 2 and the depth T of the free space 25, as shown in FIG. 1. The following condition applies for such a clamping effect:

$X > H - T$

Figure 3:
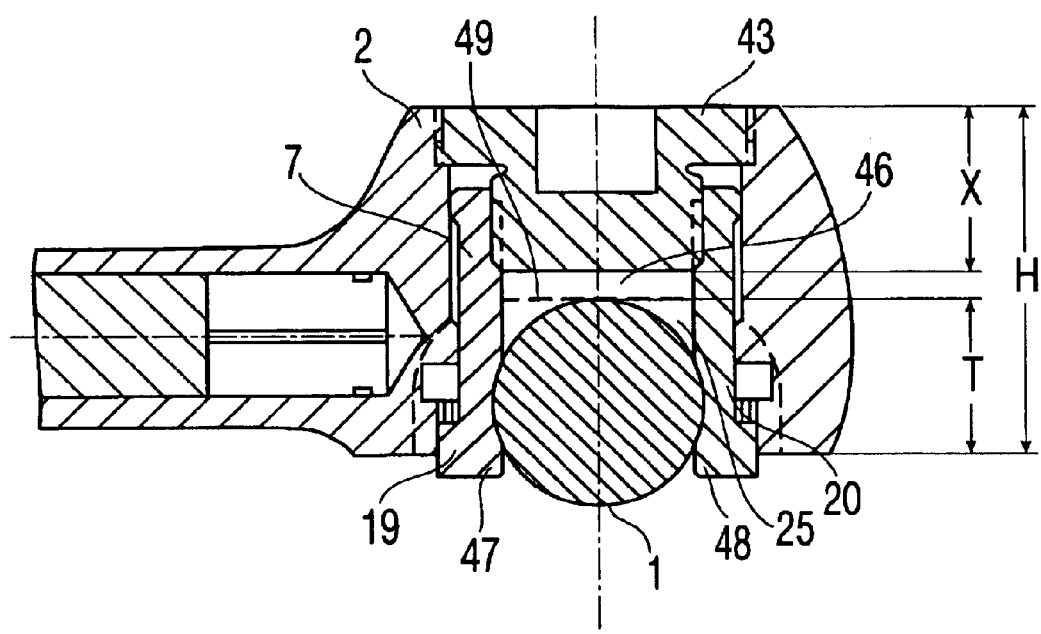
FIG. 3 shows a section through a further variant of the embodiment of the device of FIG. 1.

FIG. 3 shows an exemplary embodiment of a device according to the present invention which differs from the embodiment of FIGS. 1 and 2 in that only upper limitation 49 of free space 25 abuts longitudinal member 1, which is also pressed against elevations 47, 48 on side walls 19, 20 of clamping body 7. In order that upper limitation 49 of free space 25 presses against longitudinal member 1, rather than end 46 of locking screw 43, the connecting body 2 and locking screw 43 are designed in such a way that locking screw 43 penetrates into connecting body 2 only by a length X which is less than the dimension Y obtained from the difference between the height H of connecting body 2 and the depth T of the free space 25, as shown in FIG. 3. The following condition applies for this clamping effect:

$X < H - T$

Figure 4:
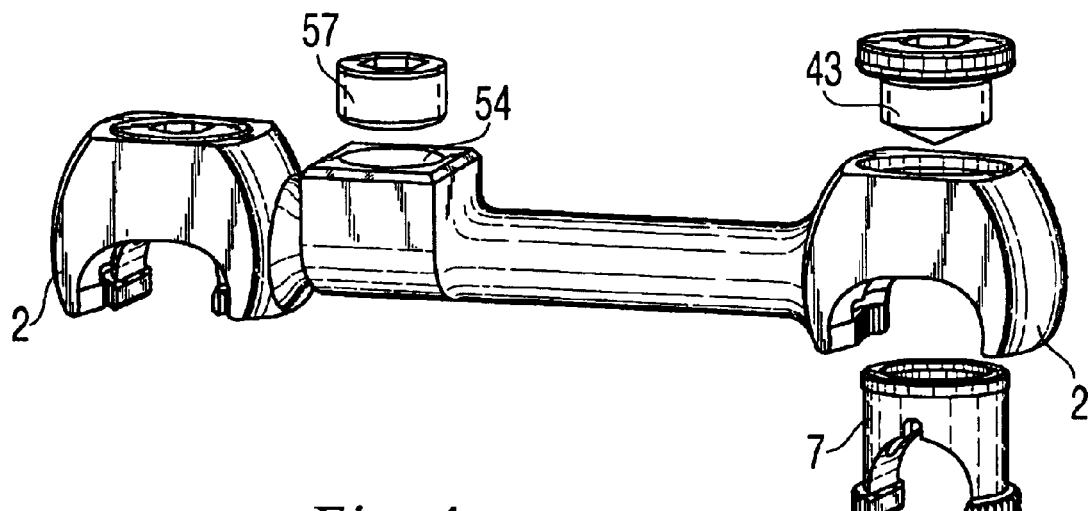
FIG. 4 shows a perspective view of a further embodiment of a device according to the present invention.
Figure 5:
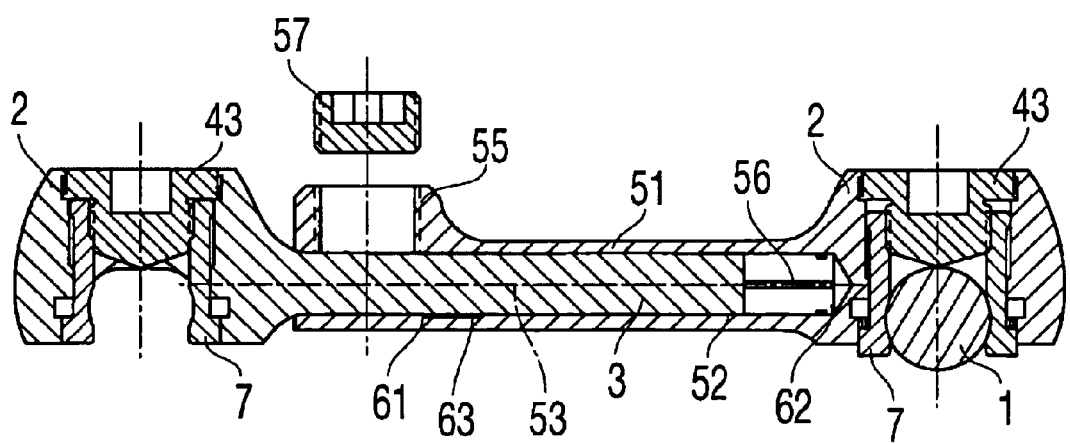
FIG. 5 shows a section through the embodiment of the device of FIG. 4.

An exemplary embodiment of a transverse connector between two longitudinal members 1 according to the present invention is shown in FIGS. 4 and 5. In this exemplary embodiment, the transverse connector comprises two connecting bodies 2 each provided with a clamping body 7 and locking screw 43. The two connecting bodies 2 are connected to one another by transverse rods 3, 51 which can be telescoped with respect to one another. The outer transverse rod 51 is formed as a hollow cylinder having a bore 52 with a longitudinal axis 53. Bore 52 is dimensioned in such a way that an inner transverse rod 3 can slide therein and can be displaced along longitudinal axis 53. Moreover, transverse rod 51 is provided with a bore 54 disposed transverse to longitudinal axis 53 and provided with an internal thread 55. A fixing screw 57 may be threadably associated with internal thread 55 such that the axial positions of transverse rods 3, 51 along longitudinal axis 53 may be locked with respect to each other. Proximate the free end of inner transverse rod 3, and remote from connecting body 2, four slits 56 are provided and disposed over the cross-section of rod 3 so that in this region inner transverse rod 3 may be resiliently biased transverse to longitudinal axis 53. Similarly, stops 62 may be provided at the free end of inner transverse rod 3, in the form of protrusions in the shape of sectors of a ring, which have a larger diameter than the remaining diameter of transverse rod 3 and which are resilient transverse to longitudinal axis 53. A relief 63 is provided in bore 52 of outer transverse rod 51 toward connecting body 2, so that when the length of the transverse connector is increased by telescoping transverse rods 3, 51 apart, stops 62 snap into relief 63. When transverse rods 3, 51 are telescoped apart so that stops 62 abut end face 61 of relief 63, further increases in length of the transverse connector and detachment of transverse rods 3, 51 with respect to each other may be prevented.

Figure 6:
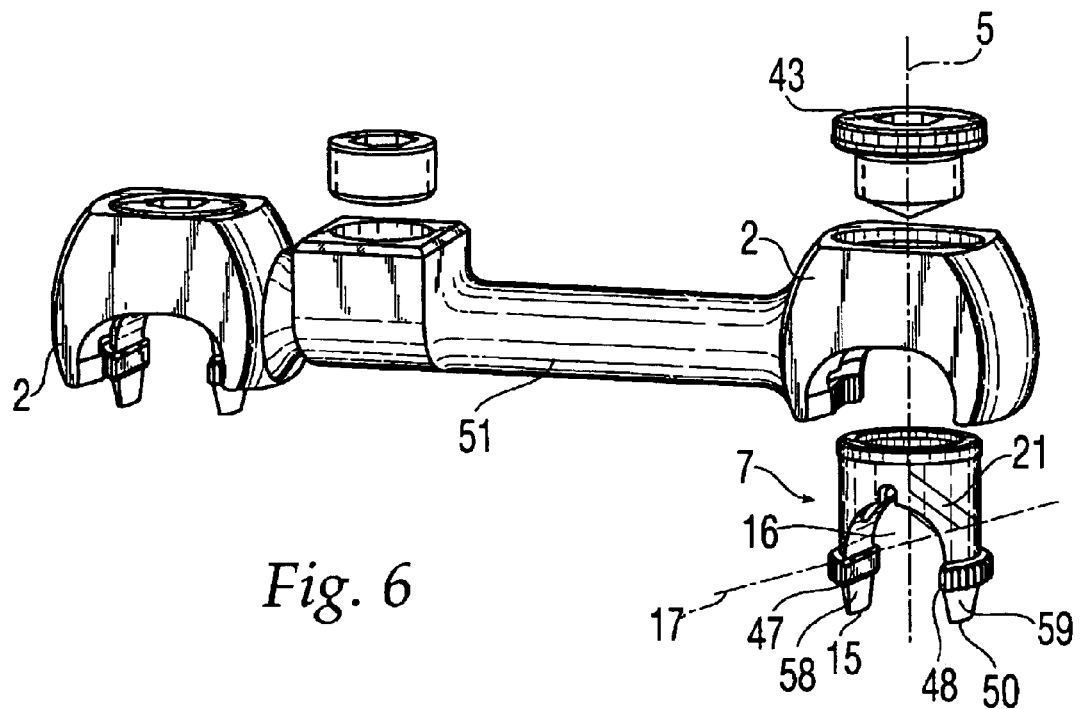
FIG. 6 shows a perspective view of a further embodiment of a device according to the present invention.
Figure 7:
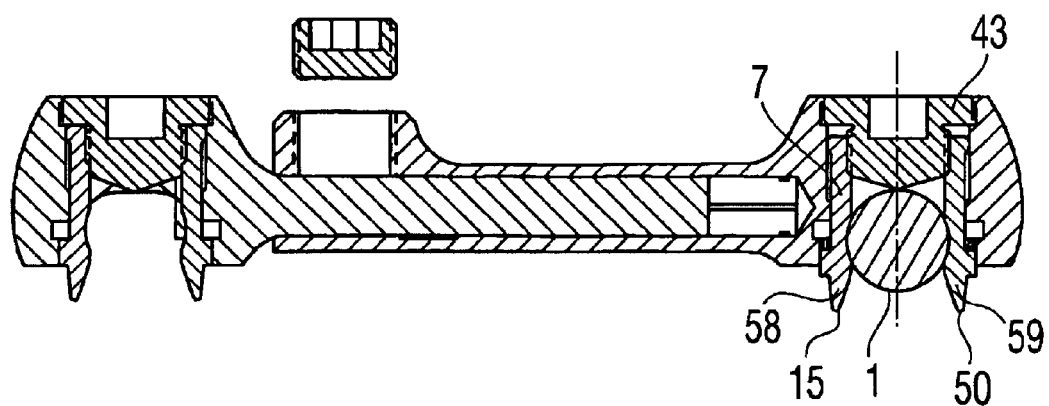
FIG. 7 shows a section through the embodiment of the device of FIG. 6.

The exemplary embodiment shown in FIGS. 6 and 7 differs from the exemplary embodiment shown in FIGS. 4 and 5 only in that clamping body 7 is provided with centering jaws 58, 59 extending from portion 40 to free ends 15, 50. Centering jaws 58, 59 are shaped such that the cross-section of through-opening 16 narrows toward central axis 5 from free ends 15, 50 toward elevations 47, 48. Moreover, in a longitudinal section running parallel to the plane 21, centering jaws 58, 59 taper toward free ends 15, 50. Thus, when a longitudinal member 1 is inserted in through-opening 16, the clamping body 7 is turned about central axis 5 such that longitudinal axis 17 of through-opening 16 is aligned parallel to the axis of longitudinal member 1.

Figure 8:
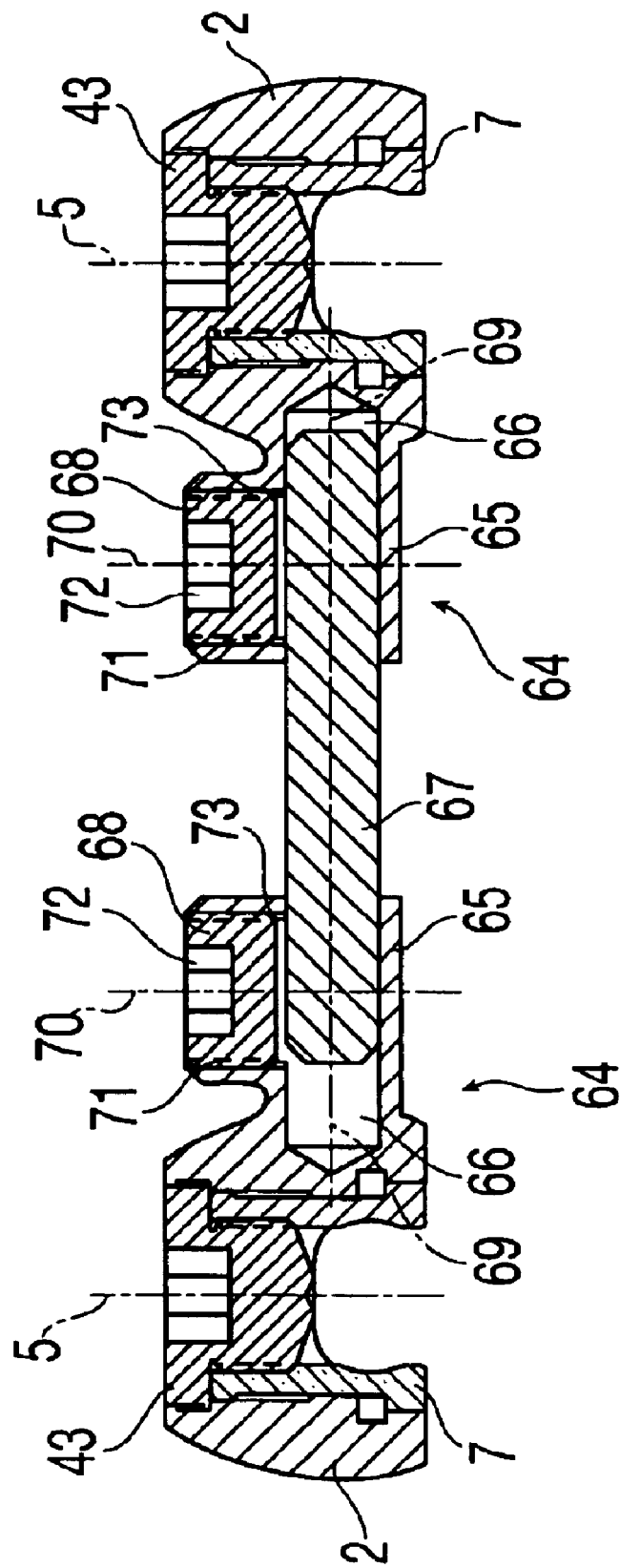
FIG. 8 shows a section through a further embodiment of a device according to the present invention.

Another exemplary embodiment of a device according to the present invention is shown in FIG. 8, and comprises two connecting bodies 2 connected by a rod 67, each connecting body 2 also provided with a locking screw 43 and a clamping body 7. The two connecting bodies 2 differ from that shown in FIG. 1 only by the design of coupling means 64. In the exemplary embodiment of FIG. 8, coupling means 64 comprises a sleeve 65 provided with a bore 66 disposed perpendicular to central axis 5. Bore 66 is formed as a blind hole having a longitudinal axis 69. A rod 67 can be inserted into bore 66 such that two connecting bodies 2 can be connected to one another and aligned along axis 69. In order to fasten rod 67 in bore 66, the sleeve 65 is provided with a bore 73 having an internal thread 71. Bore 73 is disposed on a longitudinal axis 70 that runs transverse to longitudinal axis 69 and intersects it. A stud bolt 68 may be threadably associated with internal thread 71, and stud bolt 68 may thus abut rod 67 so that rod 67 is positionally fixed within bore 66. Stud bolt 68 is provided with a hexagon socket 72 to facilitate tightening and loosening thereof. Since rod 67 can be displaced in bores 66 of connecting bodies 2, the distance between the connecting bodies 2 can be adjusted within certain limits. The device according to FIG. 8 may be equipped with clamping bodies 7 according to FIG. 1 or according to FIGS. 6 and 7.

What is claimed is:

1. A device for connecting at least one longitudinal spinal rod, the device comprising:
   a connecting body having a pair of opposed sidewalls extending therefrom defining an opening therebetween; and a through-bore disposed about a central axis oriented substantially transverse to the opening;
   a clamping body sized and configured to be received in the through-bore of the connecting body, the clamping body having a pair of opposed resilient side walls extending therefrom defining a rod receiving recess therebetween sized and configured to snap onto and initially retain the spinal rod in order to resist removal thereof generally in the direction of the central axis; the clamping body further including an internally threaded through-bore disposed about the central axis; and
   an external threaded fastener sized and configured to engage the internally threaded through-bore; wherein rotation of the fastener moves the clamping body into the through-bore of the connecting body to secure the position of the spinal rod with respect to the device.

2. The device of claim 1, wherein the rod receiving recess of the clamping body defines a rod engaging surface which contacts approximately 200° to about 250° of the outer circumference of the spinal rod.

3. The device of claim 1, wherein the rod receiving recess of the clamping body defines a rod engaging surface which contacts approximately 210° to about 240° of the outer circumference of the spinal rod.

4. The device of claim 1, wherein the connecting body and the clamping body are positively engageable with respect to each other by serrated surfaces.

5. The device of claim 1, wherein the connecting body has a first end and a second end disposed about the central axis, with the fastener received in the first end and the clamping body received in the second end.

6. The device of claim 5, wherein:
   the fastener is provided with a head having a first portion proximate the external threads and a second portion remote from the external threads, the first portion having a greater diameter than the second portion;
   the through bore of the connecting body is provided with a relief disposed proximate the first end;
   wherein the first portion of the head mates with the relief to resist removal of the fastener from the through bore in the general direction of the central axis.

7. The device of claim 5, wherein the connecting body has a first height defined parallel to the central axis between the ends, and the opening of the connecting body has a second height defined parallel to the central axis between an uppermost limitation of the opening and the second end, wherein the fastener has a length greater than the difference between the first height and the second height.

8. The device of claim 5, wherein the connecting body has a first height defined parallel to the central axis between the ends, and the opening of the connecting body has a second height defined parallel to the central axis between an uppermost limitation of the opening and the second end, wherein the fastener has a length less than the difference between the first height and the second height.

9. The device of claim 1, wherein the rod receiving recess of the clamping body has a circular cross-section.

10. The device of claim 9, wherein the clamping body has a first end and a second end, the first end defining an open region between the resilient side walls of the clamping body the open region having a first length extending between the resilient side walls, the clamping body having a second maximum length extending between the resilient side walls at a location other than at the open region, the first length is between about 85% to about 98% of the second length.

11. The device of claim 10, wherein the first length is between about 92% to about 98% of the second length.

12. The device of claim 1, wherein each of the resilient side walls has a free end provided with a protrusion thereon, the protrusions opposing each other.

13. The device of claim 12, wherein the protrusions are wedge-shaped.

14. The device of claim 1, further comprising a coupling disposed on a longitudinal axis oriented transverse to the central axis for connecting to a rod.

15. The device of claim 14, wherein the coupling comprises a sleeve with a central bore disposed about the longitudinal axis.

16. The device of claim 15, wherein the coupling further comprises a fastener bore disposed transverse to the longitudinal axis, and a fastener that is received in the fastener bore for fixing the rod in the central bore.

17. The device of claim 1, further comprising a transverse rod coupled to the connecting body transverse to the central axis.

18. The device of claim 1, wherein the resilient side walls of the clamping body each have a free end with a centering jaw thereon.

19. The device of claim 18, wherein the centering jaws are configured and dimensioned to taper the rod receiving recess of the clamping body proximate the free ends.

20. The device of claim 1, comprising a first device and a second device, wherein the first device includes an inner transverse rod and the second device includes an outer transverse rod having an internal bore sized and configured to receive the inner transverse rod so that the inner transverse rod is telescopic with respect to the outer transverse rod.

21. The device of claim 1, comprising two devices, wherein each device is provided with a coupling having a bore disposed on a longitudinal axis oriented transverse to the central axis, wherein the devices are coupled by a rod received in each of the bores on the longitudinal axis.

22. The device of claim 1, further comprising a coupling disposed on a longitudinal axis oriented transverse to the central axis for connecting the device to a bone anchorage element.

23. The device of claim 1, further comprising a coupling disposed on a longitudinal axis oriented transverse to the central axis for connecting the device to a pedicle screw.

* * * * *